United States Patent [19]

Holtman

[11] Patent Number: 4,536,432
[45] Date of Patent: Aug. 20, 1985

[54] STABILIZED ABSORBENT STRUCTURE AND METHOD OF MAKING SAME

[75] Inventor: Dennis C. Holtman, Flemington, N.J.

[73] Assignee: Personal Products Co., Milltown, N.J.

[21] Appl. No.: 601,755

[22] Filed: Apr. 18, 1984

[51] Int. Cl.³ .......................... D21C 3/20; C07D 5/22
[52] U.S. Cl. .................................... 428/171; 428/198;
428/296; 428/288; 162/72; 162/77; 162/158; 604/374
[58] Field of Search .................. 162/72, 77, 158, 206;
604/374–376; 428/171, 296, 198

[56] References Cited

U.S. PATENT DOCUMENTS

| 2,070,585 | 2/1937 | Dreyfus | 162/77 X |
| 2,106,797 | 2/1938 | Dreyfus | 162/77 X |
| 2,560,638 | 7/1951 | Dreyfus | 162/77 X |
| 2,772,968 | 12/1956 | Grondal et al. | 162/77 |
| 3,442,753 | 5/1969 | Burkart | 162/77 X |
| 3,692,622 | 9/1972 | Dunning | 428/171 |
| 3,950,219 | 4/1976 | Levesque | 162/183 X |
| 4,047,531 | 9/1977 | Karami | 604/374 |
| 4,120,747 | 10/1978 | Sarge, III et al. | 162/117 |
| 4,215,692 | 8/1980 | Levesque | 604/374 |

Primary Examiner—George F. Lesmes
Assistant Examiner—Nancy A. B. Swisher
Attorney, Agent, or Firm—Martha A. Michaels

[57] ABSTRACT

An absorbent batt of non-delignified fibers is stabilized by applying a lignin solvent to an assemblage of such fibers to soften at least 10 percent of the fibers. When the fiber assemblage is compressed and the solvent is removed, the softened lignin of adjacent contacting fibers cause a lignin-to-lignin interfiber bond to occur at the fiber intersection.

10 Claims, 3 Drawing Figures

U.S. Patent    Aug. 20, 1985    4,536,432
FIG. 1
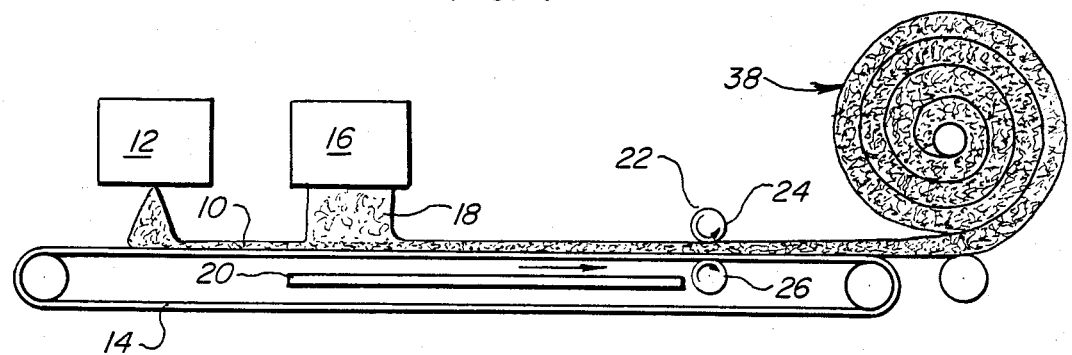
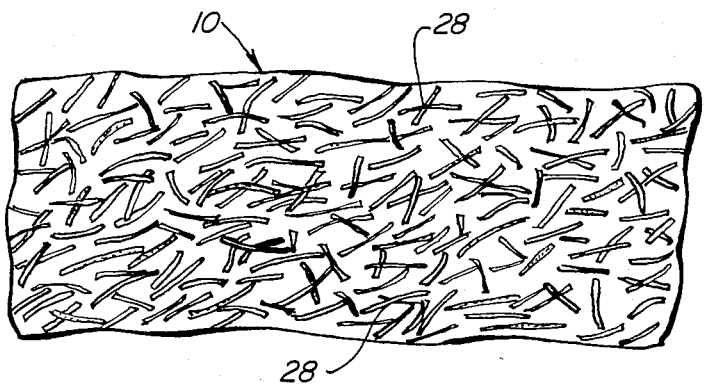
FIG. 2
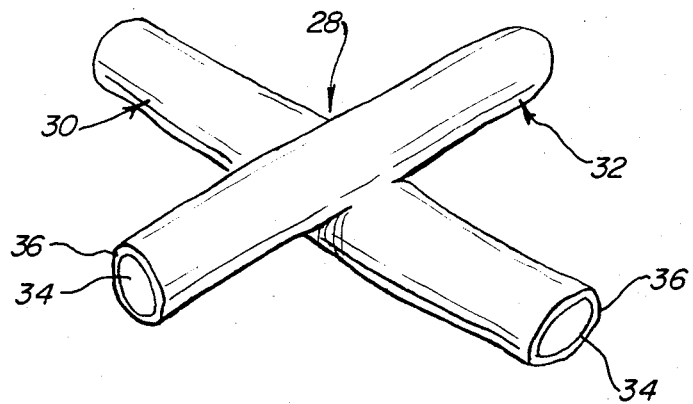
FIG. 3

STABILIZED ABSORBENT STRUCTURE AND METHOD OF MAKING SAME

TECHNICAL FIELD

This invention relates to an absorbent structure for use in diapers, sanitary napkins, and the like. More particularly, the invention relates to an improved absorbent structure including non-delignified wood pulp fibers.

BACKGROUND OF THE INVENTION

For many years it has been well known to employ natural wood pulp fibers in the manufacture of the absorbent pad or core of disposable products such as diapers, sanitary napkins, surgical dressings, and the like. In the most general sense, there are but two basic processes, chemical and mechanical, for producing pulp fibers from natural wood. The characteristics of the pulp produced by the two basic processes differ considerably and, depending upon the intended final use to be made thereof, each has certain advantages and disadvantages.

In chemical wood pulping, there is a total or partial digestion and removal of the hydrophobic constituents of the wood, such as, lignin, carbohydrates and other nonligneous materials. The yield of chemical plup is predictably low and expensive, on the order of around 50%.

Mechanical pulping processes are more cost efficient, producing yields on the order of 90% and higher. Understandably, mechanical wood pulp, sometimes known as refiner pulp, is substantially hydrophobic due to the presence of lignin and other non-absorbing materials.

More recently, there has been increasing use of wood pulp produced by thermo-mechanical processes. Thermo-mechanical pulp (TMP) is essentially mechanical pulp, but has modified qualities because of an additional heating step. The thermomechanical process involves a step of first heating the wood chips to about 270° F., usually with steam, to soften them for further mechanical processing. This heating stage tends to soften but not remove the lignin and also to loosen the individual wood fibers to ease actual defibration. Thermo-mechanical pulp thus has somewhat longer fibers than plain refiner pulp and produces structures of higher loft and greater flexibility.

Non-delignified wood pulp fibers, such as the thermo-mechanically produced wood pulp fibers, refiner produced wood pulp fibers, or the like, have become quite important in the last few years. These wood pulp fibers, also referred to as "high yield" wood pulp fibers, have become increasingly important for several reasons. The processes used to produce the fibers not only utilize more of the raw material than typical chemical processes, but the non-delignified wood pulp processes also reduce the environmental problems caused by chemical processing. Specifically, the "high yield" processes cause considerably less air pollution and water pollution than do the counterpart chemical processes. These various factors and the concomitant economic considerations make the high yield processes, such as the thermomechanical pulp process, very attractive.

Non-delignified wood pulp processes have been known for some time and are usually developed primarily for paper grade wood pulps, newsprint, and the like. These wood pulps have not been well accepted in absorbent type products, such as sanitary napkins, disposable diapers, and the like, primarily because of their relatively poor performance as the absorbent core for such products.

Conventional chemically processed wood pulp fibers have a degree of cohesive strength when placed in an air-laid web structure. Typically chemically processed wood pulp fibers are somewhat collapsed and appear in ribbon-like form. This form permits fiber entanglement during the air-laid web processing and hence results in a web having a degree of cohesiveness and fibrous web integrity.

In contrast, the non-delignified wood pulp fibers are non-collapsed, stiffer and more resilient. Webs formed of these fibers, although possessing a greater potential liquid holding capacity, have poor integrity and hence tend to break apart.

Furthermore, absorbent structures made from non-delignified wood pulp fibers are substantially hydrophobic and not readily wettable. For any absorbent structure to be satisfactory, it is highly desirable for the structure to (1) readily accept liquid, (2) easily transport the liquid from one portion of the structure to another, and (3) hold the liquid accepted.

Various techniques have been developed or suggested for improving the absorbent characteristics of non-delignified wood pulp, such as removing the fines from the wood pulp product or providing various solvent or other chemical treatments to the wood pulp product to both bleach the pulp and improve its absorbency. However, these techniques increase the economics or cost of the wood pulp and, in some instances, increase the pollution problem and, hence, do not take full advantage of the non-delignified wood pulp process.

Development of the use of mechanical wood pulp and thermo-mechanical pulp and some of the problems encountered in such use may best be appreciated by reference to some illustrative prior art examples. In "Mechanical Pulp In Absorbent Qualities", published by The Norwegian Pulp and Paper Institute (Sept., 1973) E. Bohmer et al describe the possible use of plain refiner or thermo-mechanical pulp in place of chemical pulp on a basis of cost, but conclude that it cannot achieve the liquid-holding capacity of chemical pulp. In "Thermo-Mechanical Pulp For Diapers, Other Absorbent Products" (Nov. 1975) Weyerhaeuser Company describes its new thermo-mechanical process for making pulp called Eco-Fluff and some of its potential uses. Among U.S. Patents: U.S. Pat. No. 4,047,531 teaches a two-layer pad, one of mechanical or thermo-mechanical pulp and the second of thermo-mechanical or chemical pulp; U.S. Pat. No. 4,120,747 teaches an absorbent paper made of thermo-mechanical or chemi-thermo-mechanical pulp; and U.S. Pat. No. 4,215,692 teaches an absorbent structure comprising a mixture of mechanical wood pulp (thermo-mechanical or refiner) and peat.

Other techniques for developing absorbent products utilizing non-delignified wood pulps have been suggested. One technique is disclosed in British Pat. No. 1,500,053 and uses fibers of specific measurement; that is, length and diameter. The surface-hydrophilicity of the fibers is increased by bleaching and the hydrophilic fibers are air-laid in web form and compressed to a specific density. Bleaching followed by compression substantially increases the wettability of the otherwise hydrophobic structure, but at the same time, reduces the liquid holding capacity of an absorbent structure made from non-delignified wood pulp fibers.

As mentioned above, for any absorbent structure to be satisfactory, it is not only necessary for the structure to hold liquid but also to readily accept liquid and transport it. The liquid holding capacity of the absorbent structure relates to the pore size of the fibrous bed and the wet bending modulus of the fibers. If the pore size (i.e., the spaces surrounding the fibers) is large and the wet bending modulus (i.e., stiffness) of the fibers is high, then the structure will have a relatively high liquid holding capacity but generally does not transport (wick) liquid readily. On the other hand, if the pore size is smaller and the bending modulus relatively low, the structure readily wicks liquid but will have a lower liquid holding capacity.

The fibers from the non-delignified wood pulp process can provide an absorbent structure having a large pore size and a high wet bending modulus of the fibers, however, such absorbent structures do not readily accept liquid, nor will the structure be readily densified or embossed to promote wicking.

As indicated by the cited illustrative references, the numerous efforts in this highly developed art to provide an absorptive structure utilizing cost efficient and desirable thermo-mechanical pulp are beset with difficulties that remain unsolved. These difficulties are partially or completely overcome by the present invention.

SUMMARY OF THE INVENTION

In the broadest sense the invention comprises a single layer absorbent batt made of an assemblage of non-delignified fibers, such as thermo-mechanical pulp (TMP) fibers. Improved strength and stability are imparted to the batt without the use of an extraneous binder by creating interfiber bonds between the non-delignified fibers. To this end, the assemblage of fibers is treated with a lignin solvent, which softens at least 10 percent of the lignin present in the assemblage of fibers. It should be understood that some of the lignin of the fibers may be dissolved when processed in accordance with the present invention, but that this is not necessary to achieve the batt stabilizing result, which can be accomplished by merely softening at least 10 percent of lignin of the fibers. The term "soften" or "softening" as used herein, and in the appended claims, is intended to mean that the lignin in a fiber is rendered sufficiently viscous and tacky so as to merge with and cohere to similarly viscous and tacky lignin of an adjacent fiber at a fiber intersection therebetween to thereby create an interfiber bond.

After the solvent has been applied to the assemblage of fibers to effect softening of the lignin the assemblage is compressed until the interfiber bonds are set. While volatile solvents are preferred for ease of processing, such solvents are not deemed critical to the invention. Heat is also preferably employed to accelerate the softening of the lignin and the removal of the solvent, but this is also not deemed critical to the invention.

BRIEF DESCRIPTION OF THE DRAWING

FIG. 1 is a schematic side-elevational view of a production line that may be used to practice the present invention;

FIG. 2 is an enlarged cross-sectional view of a stabilized absorbent batt formed in accordance with the present invention; and FIG. 3 is a greatly enlarged perspective view of a pair of non-delignified fibers bonded in accordance with the present invention.

DESCRIPTION OF THE PREFERRED EMBODIMENT

While this invention is susceptible of embodiment in many different forms, there is shown in the drawings and will herein be described in detail a preferred embodiment, with the understanding that the present disclosure is to be considered as an exemplification of the principles of the invention and is not intended to limit the invention to the embodiment illustrated. The scope of the invention will be pointed out in the appended claims.

The method of forming the novel absorbent batt of the present invention will be best understood from a consideration of FIG. 1. As is shown therein, an assemblage 10 of non-delignified wood pulp fibers, such as TMP fibers, is provided from a fiberizing source 12, which may take the form of a hammer mill, Fitz mill, or equivalent device. The non-delignified fibers are directed downwardly onto the upper run of an endless belt 14, it being understood that belt 14 may be a foraminous screen member and that a suction device may be disposed under the upper run of belt 14 below fiberizing device 12 to aid in deposition of the fibers on belt 14. The non-delignified fibers emanating from source 12 are of paper making length, on the order of $\frac{1}{4}$ inch or less, and the fiber assemblage 10 has insubstantial cohesive strength as initially deposited on belt 14.

As the assemblage 10 of non-delignified wood pulp fibers is moved from left to right, as viewed in FIG. 1., by belt 14, it passes to a lignin solvent applying station 16. Various different techniques, all of which are well known to those skilled in the art, may be employed at station 16 to apply lignin solvent 18 to the assemblage 10 of non-delignified wood pulp fibers. For example, the solvent 18 may be applied by printing, spraying or by saturating the assemblage of non-delignified fibers as it passes through the solvent applying station 16. The flow rate of the fiber assemblage 10 through the solvent applying station 16 is coordinated with the volume of solvent that is applied, so that at least 10 percent of the lignin of the fibers of assemblage 10 is softened.

Various different lignin solvents may be utilized to accomplish the purposes of the present invention. The following specifically identified solvents are given by way of example, and not of limitation, since all lignin solvents that function to soften lignin, as that term has been previously defined, are suitable for the purposes of the present invention.

Generally suitable for use in the present invention are the liquid, mono and polyhydric alcohols containing up to 8 carbon atoms, inclusive; aliphatic ketones containing 3 to 7 carbon atoms, inclusive; aliphatic monocarboxylic acids containing 1 to 4 carbon atoms, inclusive; primary aliphatic diamines containing up to 4 carbon atoms, inclusive; heterocyclic ethers; and the like.

Illustrative of the suitable monohydric alcohols are the lower aliphatic alcohols containing 1 to 4 carbon atoms, inclusive, e.g., methanol, ethanol, n-propanol, i-propanol, and the butanols.

Illustrative of the suitable polyhydric alcohols are the glycols, e.g., ethylene glycol, propylene glycol, triethylene glycol, etc., containing up to 8 carbon atoms, inclusive.

Illustrative of the suitable aliphatic ketones are acetone, methyl ethyl keytone, diethyl ketone, etc.

Illustrative of the suitable aliphatic monocarboxylic acids are formic acid, acetic acid, propionic acid, butyric acid, etc.

Illustrative of the suitable primary aliphatic diamines are ethylene diamine, 1,2-propanediamine, etc.

Illustrative of the suitable heterocyclic ethers are n-methyl morpholine oxide and the like.

Particularly preferred lignin solvents for the purposes of the present invention are the highly volatile solvents such as acetone, methanol, ethanol, and the like.

As will be clear to those skilled in the art, the solvent 18 may be applied to the fiber assemblage in a solvent vehicle, such as a diluent.

After the solvent 18 has been applied to the assemblage 10 of non-delignified fibers and the required lignin softening has occurred, the solvent is removed from the fiber assemblage. The specific means that is utilized to remove the solvent 18 will depend upon the physical properties of the specific solvent that is utilized, and the solvent removal means is illustrated schematically at 20 in FIG. 1. Techniques and devices for removing the solvent from the fiber assemblage include heating, suction, filtering, centrifuging, etc., as will be well understood by those skilled in the art. The term "remove" as used herein and in the appended claims is intended to encompass and include less than 100 percent removal of the solvent, since ordinarily a minor percentage of solvent residue will remain on the fibers.

After the solvent 18 has been applied to soften the lignin of the non-delignified fibers, the fiber assemblage passes to a compressing station 22 where the fiber assemblage is subjected to compressive forces to set the interfiber bonds. The compressive forces may be applied to the fiber assemblage 10 by passing it between the nip of one or more sets of calendering rolls 24 and 26. Alternatively and preferably, the fiber assemblage is passed between the nip of one or more sets of embossing rolls to provide a compacted, lower density, smaller capillary wicking pattern in the batt, such as longitudinally extending embossed lines. Calendering and embossing can both be employed, if desired. While the schematically illustrated solvent removal means 20 has been shown as extending between the solvent applying and compressing stations, it will be understood that solvent is present in sufficient quantity in the fiber assemblage at the compressing station to maintain the desired degree of linguin tack for formation of reliable interfiber bonds. In other words, the solvent removal step can be initiated prior to the compression station, and completed subsequent thereto.

With reference to FIG. 3, which is a schematic representation of a typical interfiber bond 28 formed in accordance with the present invention, it will be seen that the non-delignified fibers 30 and 32 each have a core 34, which is primarily cellulose, and a sheath 36, which is primarily lignin, as is typical of fibers such as thermomechanical wood pulp fibers. When a solvent of the type described above is applied to the fiber assemblage, the solvent removed, and the fiber assemblage compressed, adjacent fibers are brought into contact with one another. The tacky and somewhat viscous lignin on the surfaces of the contacting fibers coheres at the fiber intersection, and the softened lignin from each contacting fiber flows together and merges to form an indistinguishable lignin mass bonding the contacting fibers together. Heat may be applied to assist in softening the lignin, removing the solvent, and setting of the thus formed lignin-to-lignin interfiber bonds 28.

The stabilized batt may then be wound up for storage, as is shown at 38 in FIG. 1, or may proceed directly to a production line for the formation of a sanitary napkin, disposable diaper, or other absorbent article, with which stabilized batts of the present invention may be used.

The above detailed description of this invention has been given for clarity of understanding only. No unnecessary limitations are to be understood therefrom, as modifications will be obvious to those skilled in the art.

What is claimed is:

1. The method of forming an absorbent batt comprising the steps of: providing an assemblage of non-delignified wood pulp fibers, applying a solvent to said assemblage of non-delignified wood pulp fibers to soften at least 10 percent of the lignin of said fibers; compressing said assemblage of non-delignified wood pulp fibers to cause softened portions of the lignin to form lignin-to-lignin interfiber bonds at fiber intersections; and removing the solvent from said assemblage of non-delignified wood pulp fibers.

2. The method of claim 1 wherein said solvent is a volatile solvent.

3. The method of claim 1 wherein said solvent is selected from a group consisting of alcohols, ketones, glycols and ethers.

4. The method of claim 1 wherein said solvent is removed by heating said assemblage of fibers.

5. The method of claim 1 wherein said assemblage of fibers is compressed by embossing.

6. The method of claim 1 wherein said assemblage of fibers is compressed by calendering.

7. The method of forming an absorbent batt comprising the steps of: providing an assemblage of non-delignified wood pulp fibers; applying a volatile solvent to said assemblage of non-delignified wood pulp fibers to soften at least 10 percent of the lignin of said fibers; compressing said assemblage of non-delignified wood pulp fibers to cause softened portions of the lignin to form lignin-to-lignin interfiber bonds at fiber intersections; and removing the solvent from said assemblage of non-delignified wood pulp fibers by heating the assemblage of fibers.

8. The method of claim 7 wherein said solvent is selected from a group consisting of acetone, ethanol and methanol.

9. An absorbent batt made by the method of claim 1.

10. An absorbent batt as set forth in claim 11 wherein said batt includes spaced embossed lines.

* * * * *

UNITED STATES PATENT AND TRADEMARK OFFICE
CERTIFICATE OF CORRECTION

PATENT NO. : 4,536,432

DATED : August 20, 1985

INVENTOR(S) : Dennis C. Holtman

It is certified that error appears in the above-identified patent and that said Letters Patent is hereby corrected as shown below:

Claim 10, line 57: "set forth in Claim 11" should read --set forth in Claim 9--.

Signed and Sealed this

Fifteenth Day of July 1986

[SEAL]

Attest:

DONALD J. QUIGG

Attesting Officer

Commissioner of Patents and Trademarks